United States Patent [19]

Stone et al.

[11] Patent Number: 5,217,903
[45] Date of Patent: Jun. 8, 1993

[54] MEASURING CONNECTIVE TISSUE BREAKDOWN PRODUCTS IN BODY FLUIDS

[75] Inventors: Phillip J. Stone, Chestnut Hill; Carl Franzblau, Newton; Julianne Bryan-Rhadfi, Medford, all of Mass.

[73] Assignee: Trustees of Boston University, Boston, Mass.

[21] Appl. No.: 523,587

[22] Filed: May 15, 1990

[51] Int. Cl.$^5$ .................... G01N 23/00; G01N 23/06; G01N 30/02; B01D 15/03

[52] U.S. Cl. .................................... 436/57; 436/161; 436/174; 422/70

[58] Field of Search ................... 436/57, 161, 174, 56; 422/70, 71

[56] References Cited

U.S. PATENT DOCUMENTS

| | | | |
|---|---|---|---|
| 3,659,104 | 4/1972 | Gross et al. | 436/500 |
| 3,697,638 | 10/1972 | Hansen | 436/539 |
| 3,929,410 | 12/1975 | Schloss | 436/57 |
| 4,975,378 | 12/1990 | Banerjee | 436/57 |

OTHER PUBLICATIONS

Laurent et al. "Quantitation of Elastin in Human Urine and Rat Pelural Mesothelial Cell matrix by a Sensitive Avid-Brozin Elisa for Desmosine", J. Immunol. Method, 107, pp. 1–11 (1988).

Fujimoto et al., "Analysis of Pyrdinoline, A Cross-Linking Compound of Collagen Fibers, in Human Urine", J. Biochem., 94, pp. 1133–1136 (1983).

Cotlove, "Determination of the True Chloride Content of Biological Fluids and Tissues, I Analysis by Chorine-36 Isotope Dilution", Anal. Chem., vol. 35, No. 1, pp. 95–105 (1963).

Koch et al., "Fatty Acid Analysis by Tracer Methods", J. Radioanal. Chem., vol. 35, No. 1, pp. 197–206 (1977).

Goldstein, R. A., et al., "Urinary Excretion of Elastin Peptides Containing Desmosine After Intratracheal Injection of Elastase in Hamsters", 1978, J. Clin., Invest., vol. 5, pp. 1286–1290.

Harel, S., et al., "Desmosine Radioimmunoassay for Measuring Elastin Degradation In Vivo", 1980, Am. Rev. Resp. Dis., vol. 122, pp. 769–773.

Pelham, F., et al., "Urinary Excretion of Desmosine (Elastin Cross-Links) in Subjects with PiZZ Alpha-1-Antitrypsin Deficiency, a Phenotype Associated with Hereditary Predisposition to Pulmonary Emphysema", 1985, Am. Rev. Respir. Dis., vol. 132, pp. 821–823.

Davies, S.F., "Urine Desmosine is Unrelated to Cigarette Smoking or to Spirometric Function", 1983, Am. Rev. Respir. Dis., pp. 473–475.

(List continued on next page.)

Primary Examiner—James C. Housel
Assistant Examiner—N. Bhat
Attorney, Agent, or Firm—Choate, Hall & Stewart

[57] ABSTRACT

A method for determining a connective tissue breakdown product in a body fluid from an animal includes steps of providing a standard comprising the breakdown product having a radioactive label, the standard having a known specific radioactivity, combining the standard and a sample of the body fluid, removing from the combined standard and sample a purified breakdown product fraction containing labelled breakdown product from the standard together with breakdown product from the sample, and measuring the specific radioactivity of the fraction as a measure of the quantity of the breakdown product in the sample. Also, methods for assessing a condition of a selected connective tissue in an animal in vivo, and for assessing in vivo a disease process that includes destruction of a specified connective tissue component, and for assessing in vivo the efficacy of a therapy for treatment of such a disease process, include the steps of the method for determining a connective tissue breakdown product.

21 Claims, 3 Drawing Sheets

OTHER PUBLICATIONS

Kuhn, C., et al., "Degradation of Elastin in Experimental Elastase-Induced Emphysema Measured by a Radioimmunoassay for Desmosine", 1982, Dept. of Pathology & Medicine, Washington Univ. School of Medicine, p. 115-ff.

Yamaguchi, Y., et al., "High-Performance Liquid Chromatographic Determination of Desmosine and Isodesmosine in Tissues and Its Application to Studies of Alteration of Elastin Induced by Atherosclerosis", 1987, Elsevier Science Publishers B.V., vol. 422, pp. 53-59.

Fujimoto, D., et al., "Analysis of Pyridinoline, a Cross-Linking Compound of Collagen Fibers, in Human Urine", 1983, J. Biochem., vol. 94, pp. 1133-1136.

Laurent, P., et al., "Quantitation of Elastin in Human Urine and Rat Pleural Mesothelial Cell Matrix by a Sensitive Avidin-Biotin ELISA for Desmosine", 1988, J. Immunological Methods, vol. 107, pp. 1-11.

Black, D., et al., "Quantitative Analysis of the Pyridinium Crosslinks of Collagen in Urine Using Iod-Paired Reversed-Phase High-Performance Liquid Chromatography", 1987, Analytical Biochemistry, vol. 169, pp. 197-203.

Barone, L., et al., "Alteration of the Extracellular Matrix of Smooth Muscle Cells by Ascorbate Treatment", 1985, Biochimica et Biophysica Acta, vol. 840, pp. 245-254.

Moore, S., et al., "Photometric Ninhydrin Method for Use in the Chromatography of Amino Acids", 1948, Jour. Biol. Chem., vol. 176, pp. 367-388.

Heinegard, D., et al., "Determination of Serum Creatinine by a Direct Colorimetric Method", 1973, Clin. Chem. Acta, vol. 43, pp. 305-310.

Lansing, A. I., et al., "The Structure and Chemical Characterization of Elastic Fibers as Revealed by Elastase and by Electron Microscopy", 1952, Anat. Rec., vol. 114, pp. 555-570.

Thomas, J., et al., "Degradation Products from Elastin", Nature, vol. 200, pp. 651-652.

Starcher, B., et al., "Determination of the Elastin Content of Tissues by Measuring DEsmosine and Isodesmosine", 1976, Anal. Biochem., vol. 79, pp. 11-15.

Stone, P. J. et al., "Elastin in a Neonatal Rat Smooth Muscle Cell Culture has Greatly Decreased Susceptibility to Proteolysis by Human Neutrophil Elastase, An In Vitro Model of Elastolytic Injury", 1987, In Vitro Cel. & Dev. Biology, vol. 23, p. 633-ff.

MEASURING CONNECTIVE TISSUE BREAKDOWN PRODUCTS IN BODY FLUIDS

This invention was made in the course of work supported in part by funds provided by the U.S. Government, and the Government has certain rights in the invention.

BACKGROUND OF THE INVENTION

This invention relates to measuring connective tissue breakdown products in a body fluid from an animal.

A breakdown of connective tissue components is believed to be a component of the pathogenesis of some chronic diseases. In chronic obstructive pulmonary disease ("COPD") and in cystic fibrosis ("CF"), for instance, the elastase load in the lungs is increased, and elastin destruction in the lungs is believed to be an ongoing part of the disease process; and proteolytic digestion of lung elastin is thought to be a primary event of the alveolar wall destruction that occurs in the pathogenesis of pulmonary emphysema. In one hypothesis, a sensitive assay for elastin degradation products in urine or blood might provide an indication of the process of alveolar wall destruction. Desmosine ("DES") and isodesmosine ("IDES") are the principal cross-linking amino acids in elastin. Because DES and IDES are unique to elastin, they are recognized as established markers for elastin and elastin degradation products in mammalian tissues and fluids. Moreover, DES and IDES are not metabolized, and are passed directly to the urine, and for these reasons, some attempts to monitor elastin breakdown products as an indication of the condition of the alveolar walls have been directed to measuring urinary desmosine.

Measurements of urinary desmosine ("DES") by means of radioimmunoassay ("RIA"), however, have to date failed to support an elastase-antielastase hypothesis of emphysema, suggesting to some workers a failure of the hypothesis.

SUMMARY OF THE INVENTION

We have discovered a sensitive quantitative assay for connective tissue breakdown products, and particularly for amino acid cross-linkers, employing an isotope dilution technique using radioactively-labelled breakdown products. Particularly, with reference to elastin breakdown, we have quantified urinary DES by an isotope dilution technique using $^{14}$C-lysine labelled DES to spike urine specimens, followed by column chromatography to prefractionate the urine samples to remove interfering contaminants, and high performance liquid chromatography ("HPLC") to measure the quantities of DES and IDES. Isotope dilution minimizes problems that can arise from variation in recovery, as described in more detail below.

In general, in one aspect, the invention features a method for determining a connective tissue breakdown product in a body fluid from an animal, including steps of providing a standard including the breakdown product having a radioactive label at a known specific radioactivity, combining the standard with a sample of the body fluid, removing from the combined standard and sample a purified breakdown product fraction containing labelled breakdown product from the standard together with breakdown product from the sample, and measuring the specific radioactivity of the fraction as a measure of the quantity of the breakdown product in the sample.

In preferred embodiments the removing step includes treating the combined standard and sample by chromatography, more preferably by gel permeation chromatography such as by column chromatography using Sephadex, which is a dextrangel (Pharmacia), and most preferably by column chromatography using Sephadex G-15, which is a dextran gel having an exclusion volume corresponding to approximately 1,500 daltons; and the specific radioactivity measuring step includes using high performance liquid chromatography to measure the quantity in the fraction of the labelled breakdown product and the breakdown product from the sample, and using liquid scintillation counting ("LSC") to measure radioactivity; the connective tissue breakdown product is desmosine and the labelled breakdown product is radioactively labelled desmosine, or the connective tissue breakdown product is pyridinoline and the labelled breakdown product is radioactively labelled pyridinoline, or the connective tissue breakdown product is deoxypyridinoline and the labelled breakdown product is radioactively labelled deoxypyridinoline.

In another aspect, the invention features a method, including the steps for determining a connective tissue breakdown product in a body fluid from the animal, for assessing a condition of a selected connective tissue in an animal in vivo, in which the breakdown product is known to result from breakdown of the selected connective tissue.

In preferred embodiments the selected connective tissue contains elastin, or contains collagen.

In another aspect, the invention features a method, including the steps for determining a connective tissue breakdown product in a body fluid from the animal, for assessing elastolysis in an animal in vivo, in which the breakdown product is desmosine.

In another aspect, the invention features a method, including the steps for determining a connective tissue breakdown product in a body fluid from the animal, for assessing in vivo a disease process that includes destruction of a specified connective tissue component, in which the breakdown product is known to result from breakdown of the selected connective tissue component.

In another aspect, the invention features a method, including the steps for determining a connective tissue breakdown product in a body fluid from the animal, for assessing in vivo the efficacy of a therapy for treatment of a disease process that includes destruction of a specified connective tissue component, including administering the therapy and assessing the disease process in vivo.

The disease process can be, for example, a disease process of chronic obstructive pulmonary disease, or of cystic fibrosis; or of acute respiratory distress syndrome ("ARDS"), or of metastatic tumors of the lung, in which elastin breakdown may occur; or a disease process of a skin disorder, and particularly of a degenerative skin disorder, in which elastin breakdown and/or collagen breakdown may occur; or a disease process of arthritis, in which breakdown of collagen to form pyridinoline may occur, or of a bone disease such as Paget's disease or osteoarthritis, in which breakdown of bone collagen to form deoxypyridinoline may occur.

The invention provides a highly sensitive quantitative assay for specific products of connective tissue breakdown, yielding results comparable to those achieved by amino acid analysis.

The isotope dilution method is based upon the principle that the decrease in specific radioactivity of the added connective tissue breakdown product is proportional to the endogenous product present in the sample. The resulting specific radioactivity of the diluted product remains unchanged during subsequent purification steps, so that values derived by the isotope dilution method are independent of the level of recovery of the material being measured. This permits treatment of the sample in a multistep procedure, in which recovery levels can vary.

DESCRIPTION OF THE PREFERRED EMBODIMENTS

STRUCTURE OF THE ASSAY

Figure 1:
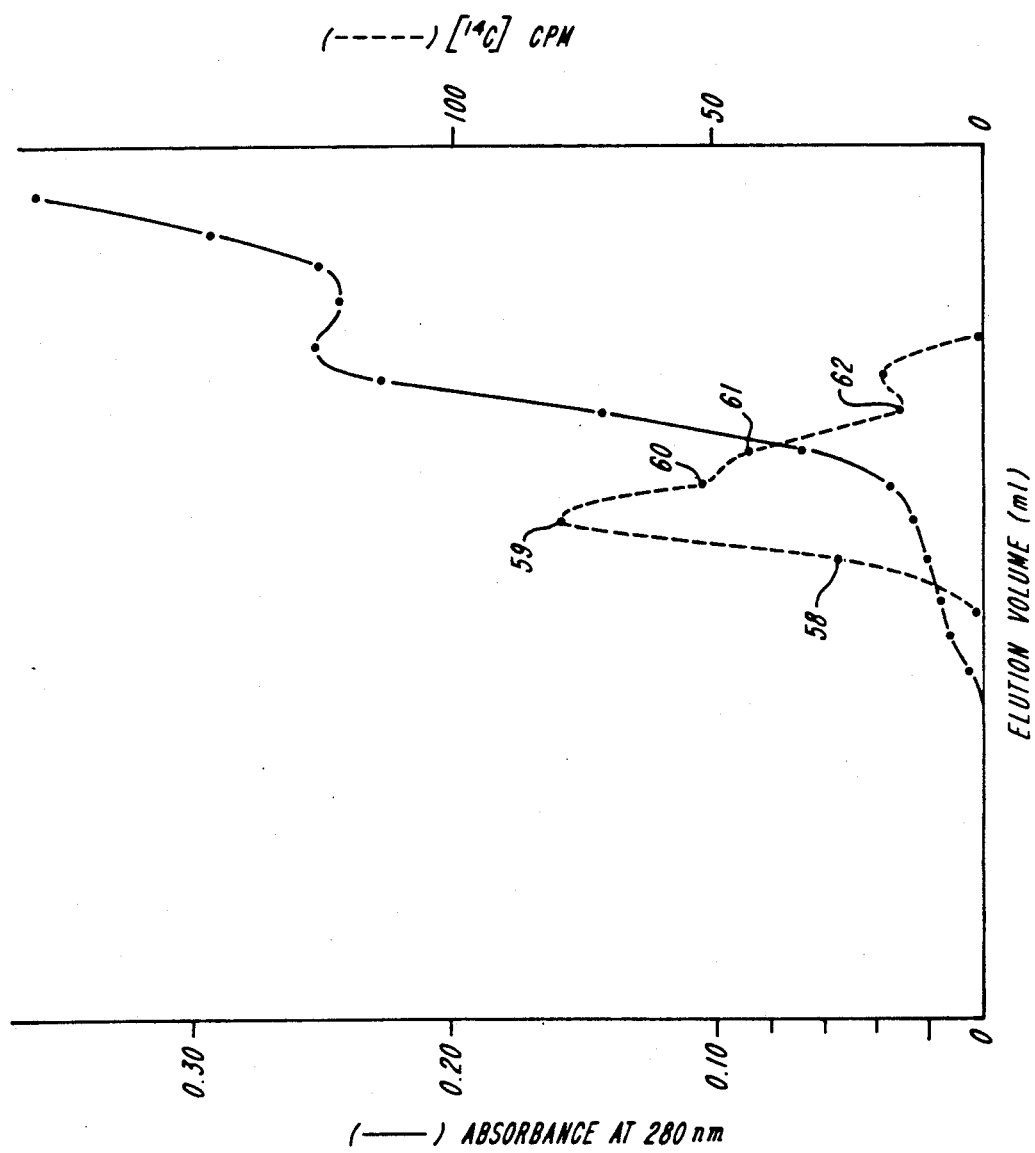
FIG. 1 is a chromatogram of a hydrolyzed $^{14}$C-DES spiked human urine sample.

Generally, the assay according to the invention includes steps of combining a standard that contains a selected radioactively labelled connective tissue breakdown product at a known specific activity with a sample of the body fluid to be assayed, purifying a fraction from the sample that contains both breakdown product from the sample and labelled breakdown product from the standard, and determining the specific radioactivity of the fraction as a measure of the amount of breakdown product in the sample.

The examples following, presented for illustration, demonstrate the use of the invention in an assay for urinary DES. Generally, urine samples were spiked with $^{14}$C-lysine labelled DES, made in smooth muscle cell cultures. Following hydrolysis of the urine, DES was purified from the urine by Sephadex G-15 chromatography, and the DES was measured using either amino acid analysis ("AAA") or, more preferably, high performance liquid chromatography ("HPLC").

The examples include assays of urine from elastase-treated hamsters, and from normal humans who have never smoked (and who are for that reason considered unlikely to have pulmonary emphysema).

The examples are now presented in greater detail, by way of illustration of preferred manners of carrying out the method of the invention.

$^{14}$C-DES and $^{14}$C-IDES preparation and amino acid analysis $^{14}$C-DES and $^{14}$C-IDES were isolated from neonatal rat smooth muscle cell cultures generally as described in Stone et al. (1987). Briefly, 1 week old T-75 flasks containing first passage cells were pulsed in the presence of serum for 24 h by addition of $^{14}$C(U)-lysine (20 uCi per flask) (New England Nuclear), after which the medium was poured off and the cultures were refed. Five weeks later the cell layers were harvested by scraping and homogenized, and elastin was isolated by a hot alkali procedure generally as described in A. I. Lansing et al. (1952), Anat. Rec., Vol. 114, pp. 555–570. The residue was hydrolyzed in 6N Hcl at 110° C. for 24 h in vacuo. An aliquot of the hydrolysate was loaded on a Beckman Model 119 CL amino acid analyzer and the eluted material was collected in 0.5 min fractions and assessed for radioactivity by liquid scintillation spectrometry, using quench correction factors as appropriate. The amino acid composition of the residue exhibited the composition of elastin described in L. M. Barone et al. (1985), Biochim. Biophys. Acta., Vol. 840, pp. 245–254. DES and isodesmosine ("IDES") eluted 4 min apart (99 and 95 min, respectively). Four lysine color equivalents were used to calculate the amount of DES and IDES present. DES plus IDES composed 0.20% of the amino acids present in the elastin. The specific radioactivity of DES and IDES were respectively 776 and 836 cpm/nmol (80% efficiency) in Ultima Gold scintillation cocktail (Packard Instruments). These values have been increased by 17% to correct for the loss of four radiolabelled carbon atoms from both DES and IDES as carbon dioxide upon reaction with ninhydrin (see, S. Moore et al. (1948), Jour. Biol. Chem., Vol. 176, pp. 367–388.

To isolate radiolabelled DES and IDES, larger aliquots of hydrolyzed rat smooth muscle cell elastin (4 mg) were loaded on the amino acid analyzer. The eluted material was not reacted with ninhydrin. Fractions were collected and assessed for radioactivity, and fractions containing DES or IDES were pooled. This procedure was repeated. The specific radioactivity of the pooled material was confirmed by loading aliquots on the amino acid analyzer, allowing the eluted material to react with ninhydrin and assessed the ninhydrin-reactive material was assessed for radioactivity as described above. Quantification of the DES and IDES in turn was confirmed using nonradioactive DES and IDES. The concentration of solutions containing DES or IDES was confirmed spectrophotometrically (see, J. Thomas et al. (1963), Nature, No. 4907, p. 651). When nonradioactive DES and IDES in amounts respectively of 1.07 and 1.08 nmol were loaded on the amino acid analyzer, 1.05 and 1.13 nmol, respectively, were recovered.

High Performance Liquid Chromatography ("HPLC")

The paired-ion $C_{18}$ reversed phase HPLC procedure, generally described in D. Black et al. (1988), Anal. Biochem., Vol. 169, pp. 197–203, for pyridinoline and deoxypyridinoline, lysine-derived collagen crosslinks, was modified as follows. Urine spiked with $^{14}$C-DES or $^{14}$C-IDES was prefractionated in 1% acetic acid as described below and combined with an equal volume of 2x loading buffer up to 1 ml. Buffers and samples were filtered and degassed before use. Samples and standards in loading buffer were applied on a 1 ml loop into a Varian model 5000 high performance liquid chromatograph equipped with a 0.46×15 cm Vydac C18 column. Solvent A was 20 mM NH$_4$Cl, Ph 3.5, containing 5 mM octane sulfonic acid (Aldrich Chemical Co.). Solvent B was 75% acetonitrile:25% Solvent A, with the concentration of octanesulfonic acid adjusted to 5 mM. The loading buffer was 100 mM ammonium acetate/Hcl, pH 3.5, containing 50 mM octanesulfonic acid. The column was developed at a flow rate of 1 ml/min as follows. The first 2 min after loading was run at 0% Solvent B; subsequently the proportion of Solvent B was increased by 1% per min to 30%, the concentration was increased to 70% B in the next 10 min and returned to 0% B in the next 8 min. Total cycle time was 52 min. The column effluent was monitored for absorbance at 275 nm. One min fractions were collected for liquid scintillation spectrometry where appropriate. Representative calculations for IDES and DES are described below with reference to Table 4.

Sample Preparation

Preparation of samples is illustrated by examples using hamsters fed standard chow and using hamsters fed a meat-free modified diet. The results are shown in Table 1, showing a comparison of HPLC and AAA 24 h DES and IDES excretion values per hamster.

TABLE 1

| Treatment | DES (ug) | | | IDES (ug) | | |
|---|---|---|---|---|---|---|
| | AAA | HPLC | AAA/ | AAA | HPLC | AAA/ |
| Example #1 | | | | | | |
| Control | 0.080 | 0.073 | 1.09 | 0.105 | 0.076 | 1.38 |
| HNE | | | | | | |
| a. | 0.158 | 0.139 | 1.14 | 0.160 | 0.138 | 1.16 |
| b. | 0.178 | 0.194 | 0.92 | 0.206 | 0.221 | 0.93 |
| Example #2 | | | | | | |
| Control | 0.075 | 0.061 | 1.23 | 0.076 | 0.067 | 1.13 |
| PPEI | 0.273 | 0.258 | 1.06 | .0.275 | 0.0256 | 1.07 |
| | | | 1.13 ± 0.07 (n = 5) | | | 1.09 ± 0.05 (n = 5) |

G-15 fractions from an individual determination were pooled. One-half of each pool was assessed by amino acid analysis and the other half by HPLC. A ratio of the two values was calculated and then the mean ratio for the 5 determinations was calculated and found not to be different from 1.0, indicating that amino acid analysis and HPLC yielded similar results.

In Example #1 hamsters (100 g) were maintained on standard 5001 Purina Rodent Laboratory Chow. Groups of 8 hamsters were anesthetized by inhalation of carbon dioxide and instilled intratracheally with 0.5 ml saline or 0.5 ml saline containing 300 ug human neutrophil elastase ("HNE") purified as described in P. J. Stone et al. (1987), In Vitro Cell. Dev. Biol., Vol. 23, No. 10. Urine was collected by placing hamsters in metabolic cages for 3 days. Sodium azide was added to each cup before collection was begun. The cups were emptied at least daily and the contents stored at $-20°$ C.

In Example #2 hamsters were maintained on Purina Modified Lab Chow, in which fish meal, meat meal, bleachable fancy tallow and dried whey were removed from standard rodent chow. To balance the latter formula with fat and protein, corn oil and RP101 soy protein isolate were added and the levels of ground corn and soybean meal were increased. Groups of 6 hamsters were instilled with 0.5 ml saline containing 300 ug HNE or 300 ug porcine pancreatic elastase ("PPE") purified as described in Stone et al. (1987). Collection of urine was initiated immediately after treatment.

For comparison, 2 control groups of 9 hamsters each, one group grown on modified chow and one on regular chow, were not instilled.

At the end of the 3 day collection period hamsters were anesthetized and studied by lavaging the lungs three times with heparin saline to remove exudate, injecting the lungs with 5 ml of fixative (4CFlG), excising and degassing lungs and measuring lung volume displacement. Three transverse sections were cut from the left lung and paraffin embedded histologic sections were stained with hematoxylin and eosin and were assessed for air space enlargement by measuring the mean linear intercept (see, P. J. Stone et al. (1990), Am. Rev. Respir. Dis., Vol. 141, pp. 47-52), herein incorporated by reference.

Before analysis the urine was centrifuged at 30,000 $\times$ g for 15 min to remove food material and other particulates. Six hamster-days of urine were pooled, usually 15-30 ml, aliquots were removed for determination of creatinine by the method described in D. Heinegard et al. (1973), Clin. Chim. Acta., Vol. 43, p. 305, using a kit (Sigma Diagnostics); a known amount of $^{14}C$-DES (around 500 cpm) was added, and the aliquot was stored at $-20°$ C. For analysis the spiked urine was combined with an equal volume of 12N Hcl and the sample was refluxed at 110° C. under nitrogen for 24 h.

The hydrolyzed sample was then dried under a stream of nitrogen gas and brought up in 10 ml of 1% acetic acid. The sample was divided in half and was loaded on two disposable columns (Biorad) packed with Sephadex G-15 in 1% acetic acid. The early eluting fractions containing $^{14}C$ radioactivity were collected, reduced to a volume of 1-2 ml with a stream of nitrogen, and loaded on a 2.6 $\times$ 100 cm column (Pharmacia) packed with Sephadex G-15 in 1% acetic acid and run at room temperature. The column had been calibrated with bovine serum albumin and $^3H_2O$ to determine $V_o$ and $V_t$, respectively. Eluted fractions were assessed for absorbance at 280 nm and radioactivity. DES eluted with a $K_{av}$ about 0.26. The column was flushed with 1% acetic acid until the effluent had no measurable absorbance at 280 nm as compared with 1% acetic acid; usually this required 5 days. The persistence of absorbance indicated the need to replace the contents of the column. In earlier demonstrations of the method column fractions containing $^{14}C$ radioactivity were pooled; 50% of the pool was analyzed by amino acid analysis ("AAA") as described above and the remainder by HPLC. After these initial studies had validated the HPLC method for quantification of DES and IDES, individual column fractions were run on the HPLC.

For demonstration of the assay for DES in human urine, human urine was collected for 24 h in the presence of 0.02% sodium azide at 2° C. from male volunteers ages 34-50 who had never smoked. Volunteers were asked not to eat red meat for 1 day before and during the urine collection. An aliquot of the urine was removed for measurement of creatinine. Other aliquots representing 10% by volume of the 24 h pool were stored at $-20°$ C. after the addition of a known amount of $^{14}C$-DES (around 500 cpm). Aliquots representing as little as 7% or as much as 15% of the 24 h pool were also assayed; results were not different. For analysis the sample was reduced in volume to a viscous orange fluid with a rotary evaporator under reduced pressure from a water aspirator. Forty ml of 6N HCl was added to the sample, which was then hydrolyzed and processed as above. More preferably, the sample can be reduced to a convenient small volume (but not to a viscous orange fluid) and then reconstituted using water and HCl to a final volume of 40 ml at 6N HCl.

For assessment of dialyzable DES and IDES, other aliquots of hamster and human urine samples were dialyzed 3 times in 1% acetic acid, followed by spiking with 500 cpm $^{14}$C-DES as above, lyophilization and hydrolysis. The hydrolyzed material was processed as above.

Comparison of DES and IDES Recoveries

Human urine samples were spiked with 500 cpm each of $^{14}$C-DES and $^{14}$C-IDES and processed as above. Sephadex G-15 fractions containing radioactivity were combined into pools, early fractions containing the peak fraction and later fractions containing lesser amounts of radioactivity. Each pool was separately loaded on an amino acid analyzer and the radioactivities eluting with DES and IDES were separately assessed and compared.

Quantification of nonradioactive DES added To urine samples

Nonradioactive DES (4.2 nmol) was added to 10% by volume to 24 h human urine samples, the samples were spiked with 500 cpm $^{14}$C-DES, and the amount of DES added was verified using the isotope dilution method after prefractionation on Sephadex G-15 and measurement using HPLC as described above.

Quantification of DES and IDES using isotope dilution of $^{14}$C-IDES

Human specimens were spiked with 500 cpm of $^{14}$C-IDES and processed as described above. Values for DES and IDES in the specimens were calculated as described above and compared with values obtained in equivalent specimens that had been spiked with $^{14}$C-DES.

Statistical analysis

Values are presented in the Tables and Figures as the mean±SE. Statistical analyses involving 2 groups were carried out using the t test for unpaired or, where noted, for paired data. Comparisons involving three groups were made using analysis of variance, the Dunnett test for comparison of groups with the control group, or the Bonferroni test for comparison among all the groups. Probability values of $p<0.05$ were considered significant.

Comparison Of IDES And DES Recoveries

The following two examples demonstrated that the % recovery of IDES and DES were not different. In a first example 147 cpm of DES and 137 cpm of IDES were recovered from the amino acid analyzer after loading the early fractions; respectively 58 cpm and 64 cpm were recovered from the late fractions or a total of 211 cpm and 195 cpm for DES and IDES, respectively, or recoveries of 42% and 39%. Including the loss of radioactivity owing to formation of $^{14}$CO$_2$ (17%) and the 150 cpm used to evaluate the radioactivity of eluted fractions, the overall recovery exceeded 60%. In a second example 153 cpm and 159 cpm of DES and IDES were recovered in the early fractions and 34 cpm and 28 cpm in the later fractions. Similar relative recoveries of DES and IDES in the early and late fractions suggested that DES and IDES co-eluted from the G-15 column; if they had not co-eluted the early fractions would be relatively enriched in either DES or IDES. Spiking the urine samples with both $^{14}$C-DES and $^{14}$C-IDES appeared to improve the recovery of radioactivity as compared with spiking the sample with either DES or IDES, suggesting that losses were not simply proportional to the amounts initially present. Thus, the losses of DES and IDES are not constant or predictable from sample to sample.

Comparison Of Results From AAA And HPLC In Hamsters

Results obtained with hamster samples that were analyzed by AAA and HPLC were compared as follows. One-half of the pool was assessed by AAA and the other half by HPLC (Table 1). A ratio was determined by dividing the DES or IDES AAA value by the corresponding HPLC value for each of 5 samples, although AAA values tended to be larger than HPLC values. The mean value for the 5 ratios was not different from 1.0 indicating that the values obtained by AAA and HPLC were not different from each other.

Values For Hamster Samples

Representative urinary DES and IDES values per hamster per day for 3 treatments: control (untreated), HNE or PPE, are presented in Table 2, which shows DES and IDES excretion values for hamsters in Example 2 of Table 1.

TABLE 2

| Treatment | DES (ug) | IDES (ug) | MLI (um) |
|---|---|---|---|
| none | 0.074 ± 0.008 (8) | 0.087 ± 0.005 (8) | 54 ± 2 (9) |
| HNE | 0.212 ± 0.012 (2) | 0.245 ± 0.019 (2) | 64 ± 2 (6) |
| PPE | 0.816 ± 0.005 (2) | 0.826 ± 0.072 (2) | 86 ± 5 (6) |

Urine for each treatment group was collected for 3 days after treatment, pooled and analyzed for DES and IDES. The lungs were fixed and the left lung was used to determine the mean linear intercept (MLI). Values are given as the mean±SE (no. of determinations). Twenty-four hour creatinine values per hamster were 2.19±0.15 (5), 1.61±0.07 (2) and 0.84±0.03 (2) mg, respectively, for untreated, HNE-treated and PPE-treated. No differences were found between untreated hamsters on meat-free chow and regular chow; data from those two groups were combined.

With doses of HNE and PPE representing nearly equimolar amounts, the DES levels in the urine were respectively 3 and 11 times those found in urine of untreated hamsters. If all of the increase in DES excretion were from the lungs, this would represent 74 and 400 ug of lung elastin, respectively, based upon 3000 ug of elastin in the lungs with an elastin amino acid composition of 0.9 residues DES per 1000 residues amino acids (see, Starcher et al. (1977)). After the 3 day urine collection HNE and PPE had produced airspace enlargements of 119% and 159% of control, respectively. Dialysis of urine from untreated or HNE-treated hamsters using dialysis tubing with a 1000 dalton cutoff removed more than 85% of the DES and IDES. With PPE treatment, use of tubing with a 2000 dalton cutoff removed 70%; a significant amount of DES and IDES peptides with molecular mass greater than approximately 2000 daltons was apparently present. There was no difference between the urinary DES values for hamsters on the regular chow and those on meat-free chow; the groups were combined for data presentation. Twenty-four h urine creatinine content of HNE- and PPE-treated hamsters was significantly decreased as compared with the untreated group as were the volumes (2.85 ml for HNE-treated, 2.0 ml for PPE-treated and 5 ml per day for untreated hamsters).

Values For Human Specimens

Three 24 h specimens obtained from volunteer #1 over a 4 month period were analyzed by AAA, AAA and HPLC, or HPLC only, respectively. There were no differences among the specimens. The values [mean±SEM (n)] were 8.3±0.1 (2) ug DES and 8.2±0.1 (2) ug IDES for the first specimen, 8.6±0.9 (5) ug DES and 7.5±1.0 (5) ug IDES for the second specimen, 6.5±1.4 (3) ug DES and 7.1±0.5 (3) ug IDES for the third specimen. The values, expressed as ug DES/g creatinine, for 4 volunteers are shown in Table 3 along with 24 h creatinine values.

There appeared to be a linear relationship between urinary creatinine and DES values, with a mean value in this preliminary study of these 4 volunteers of 4.9±0.4 ug DES/g creatinine. The variability of values obtained for a specimen using 4 sequential eluted fractions from the large G-15 column was determined, and the results are presented in Table 4. The standard error for the calculated DES and IDES values was 5 and 8% of the mean, respectively. For volunteer #2 two specimens collected 3 months apart had 24 h DES values of 8.9±0.8 (6) ug and 8.2±0.7 (6) ug. Dialysis of human urine using tubing with a 1000 dalton cutoff decreased the DES and IDES values by more than 85%.

TABLE 3

| Individual Subect (g creatinine/day) | DES (ug) | IDES (ug) |
| --- | --- | --- |
| Volunteer #1 | 4.9 ± 0.4 | 4.9 ± 0.3 |
| (1.6 g) | (n = 10) | (n = 10) |
| Volunteer #2 | 5.1 ± 0.3 | 5.0 ± 0.3 |
| (1.7 g) | (n = 12) | (n = 12) |
| Volunteer #3 | 5.6 ± 0.3 | 4.5 ± 0.2 |
| (2.0 g) | (n = 8) | (n = 8) |
| Volunteer #4 | 3.9 ± 0.3 | 3.7 ± 0.1 |
| (2.0 g) | (n = 3) | (n = 5) |

Recovery of a bolus of unlabelled DES (4.2 nmol) that had been added to a urine sample was assessed by HPLC. Excluding the DES added as $^{14}$C-DES, 6.2±0.5 (4) nmol was present in the urine sample, representing 10% by volume of the 24 h pool from volunteer #2. After subtraction of the endogenous DES determined in earlier experiments (1.7 nmol) we calculated that 4.5±0.5 nmol DES (n=4) had been added, a value that was not significantly different from 4.2 nmol DES that was, in fact, added.

The isotope dilution method gave similar results whether we used $^{14}$C-DES or $^{14}$C-IDES; calculated values for DES and IDES in specimens spiked with $^{14}$C-IDES were not different from values obtained in equivalent specimens that had been spiked with $^{14}$C-DES.

TABLE 4

| Fraction # | $^{14}$C-DES recovered (CPM) | nmol in fraction | | ug/24 h calculated | |
| --- | --- | --- | --- | --- | --- |
| | | DES | IDES | DES | IDES |
| 58 | 20 | 0.0878 | 0.0829 | 9.4 | 12.6 |
| 59 | 43 | 0.1844 | 0.1422 | 9.1 | 10.1 |
| 60 | 46 | 0.1866 | 0.1313 | 8.4 | 8.7 |

TABLE 4-continued

| Fraction # | $^{14}$C-DES recovered (CPM) | nmol in fraction | | ug/24 h calculated | |
| --- | --- | --- | --- | --- | --- |
| | | DES | IDES | DES | IDES |
| 61 | 34 | 0.1624 | 0.1064 | 10.6 | 9.5 |

For the data presented in Table 4, four sequential fractions from the final G-15 fractionation step were analyzed on the HPLC. The radioactivity present in the DES eluting from the HPLC was determined. Recovery in the 4 fractions of the radioactivity present in the initial spike (579 cpm) was 25%. Including the 56 cpm lost in determining which G-15 fractions contained $^{14}$C-DES, recovery was 34%. A representative calculation of the nmol DES and IDES present in fraction #60 is described below with respect to FIG. 2. Calculation of 24 h values based upon the results of fraction #60 are as follows. The specific radioactivity of DES in fraction #60 is 247 cpm/nmol as compared with 776 cpm/nmol for the $^{14}$C-DES used to spike the sample, 3.14×0.746 nmol was present in the sample after the spike was added or 1.60 nmol of endogenous DES (after subtraction of the 0.746 nmol representing the added DES). The sample represents 10% by volume of the 24 h pool. The molecular mass used for DES is 526 daltons, so that 1.60 nmol×526 ng/nmol×10=8.4 ug DES present in the 24 h urine. The calculation for IDES is based upon our finding of similar recoveries for DES and IDES, i.e., 46 cpm in this fraction out of a spike consisting of 579 cpm.

FIG. 1 shows a representative chromatogram of a hydrolyzed $^{14}$C-DES spiked (579 cpm) human urine sample after loading on a 2.6×100 cm column packed with Sephadex G-15 and run in acetic acid. The sample had been prefractionated on a 20 ml disposable column packed with Sephadex G-15. With a flow rate of 0.23 ml per min, 3.5 ml fractions were collected, assessed for absorbance at 280 nm (solid line) and 0.35 ml assessed for $^{14}$C radioactivity (dashed line); data points for fraction numbers 58-61 are indicated by reference numerals 58-61 in FIG. 1. After subtracting background the radioactivity values were multiplied by 10, because 10% of the 24 h urine was the aliquot taken for analysis, and by the quench correlation factor (1.05). The data for fractions ##58-61 are given in Table 4, and the HPLC chromatogram for fraction #60 (210 ml) is shown in FIG. 2.

Overall the two gel exclusion steps removed more than 99.9% of the 280 nm absorbing material, while $^{14}$C-radioactivity losses were approximately 40%. Without both chromatographic steps, material loaded on the amino acid analyzer or the HPLC produced high background absorbance so that IDES and DES were difficult to quantify. Indeed, the amount of DES and IDES in the last G-15 fraction, and sometimes the last two fractions, containing $^{14}$C-DES or $^{14}$C-IDES radioactivity were difficult to quantify because of nonspecific interference from 275 um absorbing material.

Figure 2:
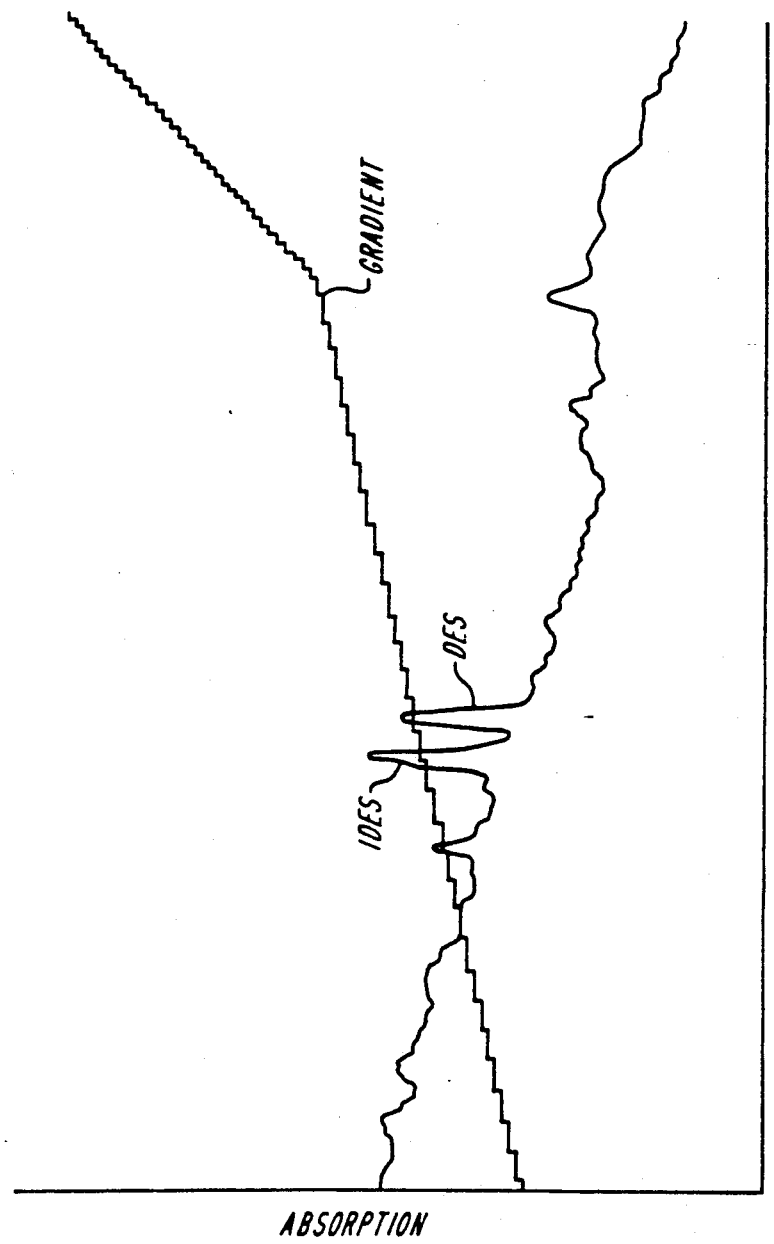
FIG. 2 is a representative HPLC chromatogram for fraction #60 from the sample shown in FIG. 1.

FIG. 2 shows a representative HPLC chromatogram of fraction #60 from the prefractionated sample of hydrolyzed human urine spiked with $^{14}$C-DES shown in FIG. 1. The full range of the y axis in FIG. 2 represents 0.05 absorbance units at 275 nm. Comparison with the HPLC peak for $^{14}$C-DES and $^{14}$C-IDES indicates the presence of 0.180 nmol DES in the peak at 23.1% B and 0.131 nmol IDES at 23.8% B. The calculation of the 24 h values is described [above] with reference to Table 4.

For fractions #62 and #63 the amount of $^{14}$C-DES recovered was low and the level of background absorbance interfered with accurate determination of the DES and the IDES peak heights.

Figure 3:
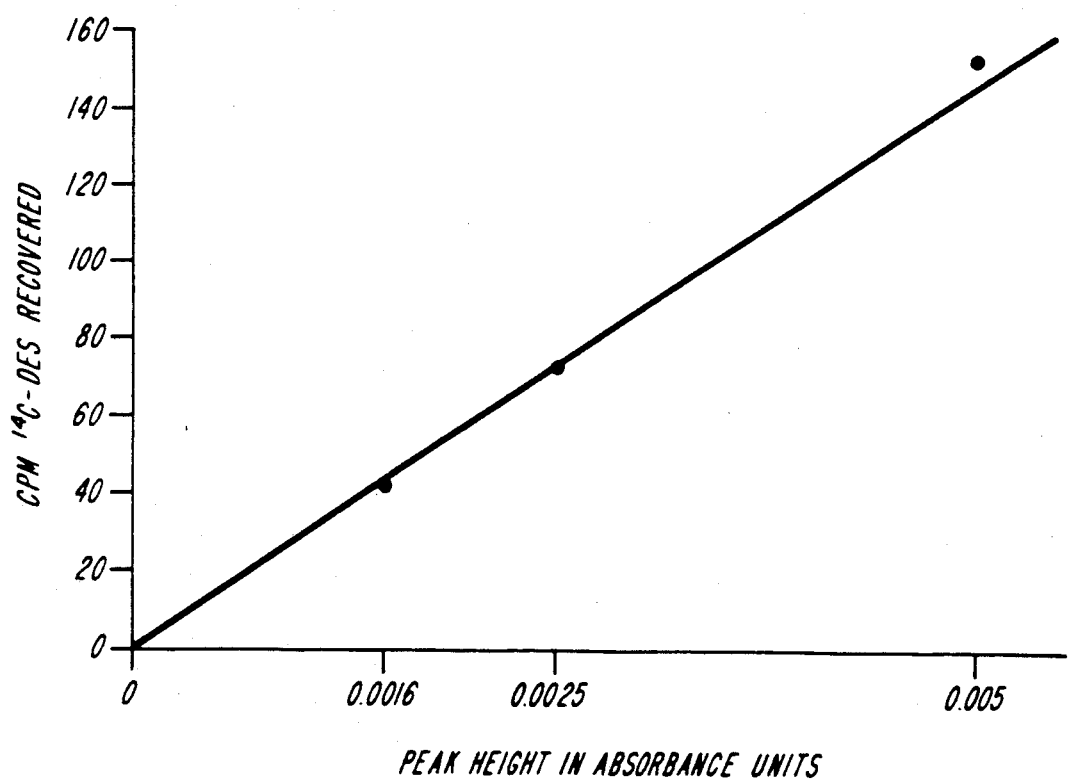
FIG. 3 is a calibration curve for $^{14}$C-DES recovered as a function of peak height on an HPLC chromatogram as in FIG. 2.

FIG. 3 shows a calibration curve for $^{14}$C-DES (cpm) recovered as a function of peak height on the HPLC. Background cpm have been subtracted. The correlation coefficient for the linear regression line shown is r less than 0.999. As FIG. 3 shows, there was a linear relationship between $^{14}$C-DES radioactivity recovered and the maximum absorbance of the DES peak when $^{14}$C-DES standards were run on the HPLC. Separation of IDES and DES in the chromatogram is 0.6 min. Using AAA well resolved peaks, 4 min apart, were obtained for IDES and DES.

Use

The method of the invention can be used for in vivo assessment of a disease process that includes connective tissue breakdown, by providing accurate quantitative determination in a body fluid of a specific product of the connective tissue breakdown. For example, DES and IDES are products specifically of elastolysis, and either DES or IDES or, even more accurately, both DES and IDES can be measured in a sample of urine for an assessment of disease processes in which elastin breakdown may occur, such as chronic obstructive pulmonary disease, or cystic fibrosis, or acute respiratory distress syndrome, or a metastatic tumor of the lung, or a skin disorder. And, for example, pyridinoline and deoxypyridinoline are specific products of collagen breakdown, and pyridinoline can be measured in the urine for an assessment of disease processes in which collagen breakdown may occur, such as arthritis (pyridinoline), or a bone disease such as Paget's disease or osteoarthritis, in which breakdown of bone collagen to form deoxypyridinoline may occur. Certain disease processes may be characterized by elevation (or depression) of the quantities of one or more connective tissue breakdown products in relation to other connective tissue breakdown products, and the method can be employed to measure more than one such breakdown product in any sample.

Urinary DES (and IDES) values did not differ for individuals when measured according to the invention on different occasions. Calculated values for endogenous DES and IDES in aliquots that had been spiked with $^{14}$C-IDES were not different from values determined using equivalent aliquots that had been spiked with $^{14}$C-DES. Values for DES and IDES in the urine were rarely more than 20% apart, reflecting the known relative DES and IDES composition of human and hamster elastin.

Because the method yields results consistent over time, it can be used to assess or monitor the efficacy of a therapeutic for a disease condition that includes connective tissue breakdown, by for example comparing a connective tissue breakdown product measurement made prior to instituting the therapy with one or measurements made during the course of or following the therapy. Such an assessment can be particularly useful where a variety of therapies are available, and where there is substantial variation in patients' responses to a particular therapy, for selection of the most efficacious therapy in a relatively short time by trial-and-error.

The assay for DES and IDES can be used to determine a person's history of smoking tobacco, particularly for actuarial purposes. Preliminary results suggest that urinary DES (and IDES) may be substantially elevated in persons who smoke tobacco as compared with persons who have never smoked; and that urinary DES (and IDES) may be to a lesser degree elevated in persons who have a prior history of smoking but who no longer smoke.

The values for DES in human and hamster urine, as determined according to the invention, are smaller by a factor of 5-10 than values reported using methods employing RIA. One explanation for this difference is that urine may contain components that can erroneously elevate values that have been determined using an antibody. Antibody preparations directed against DES can cross-react towards the collagen crosslink, pyridinoline, which is present in higher concentrations in human urine than DES; and non-specific interferences can occur in ELISA methods for determining urinary DES. Thus, for example, if as much as 90% of previously reported DES values were impurities, a doubling of DES output would have increased the measured value by only 10-20%, an amount well within the standard error of the method.

The method of urinary DES measurement according to the invention can be useful for understanding diseases such as chronic obstructive pulmonary disease ("COPD") and cystic fibrosis ("CF"), where the elastase load of the lungs is increased and elastin destruction in the lungs is believed to be an ongoing part of the disease process. A decrease in an elevated level of urinary DES associated with COPD or CF following treatment with a supplemental antielastase would be indirect evidence that the disease process had been interrupted. An elevated level of urinary DES may also be associated with severe hereditary deficiency of the elastase inhibitor alpha-1-protease inhibitor found in the PiZZ phenotype and other. This deficiency has been treated experimentally by replacement therapy for almost 10 years, but the efficacy of this treatment has not yet been determined; the invention provides for assessment of such therapies. The early diagnosis and therapy of other conditions, such as acute respiratory distress syndrome and metastatic tumors of the lung, where an elastase imbalance is thought to be present in proximity of elastic tissues, can be facilitated by measurement of urinary DES.

OTHER EMBODIMENTS

Other methods than gel permeation chromatography may be used for the removal step. However, because connective tissue cross-linking amino acids such as DES or IDES are so large in comparison to other amino acids, and because the hydrolysis step yields substantially a mixture of amino acids and other small molecules, prefractionation according to molecular size is preferred. Using Sephadex G-15, the large cross-linking amino acids elute very early and cleanly.

Other labels than $^{14}$C can be used; for example, the label can be a $\gamma$-emitter, and the activity can be measured using a $\gamma$-counter. Labelled connective tissue breakdown product can be made by culturing any cells that produce the mature (cross-linked) connective tissue, using media containing a labelled amino acid constituent of the connective tissue breakdown product, such as for example labelled lysine for production of DES and IDES. Alternatively, labelled breakdown product can be provided by means other than production in culture; for example, DES or IDES can be labelled by tritium exchange or by some other chemical method. Preferably, the label does not alter those properties of the product in such a way that the behavior of the labelled product in the prefractionation or separation steps is rendered substantially different from that of the unlabelled product.

We claim:

1. A method for quantitatively determining a connective tissue breakdown product in a body fluid from an animal, comprising providing a standard comprising the breakdown product having a radioactive label, combining a known quantity of said standard, containing a known quantity of said label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step.

2. The method of claim 1 wherein said substantially purifying step comprises treating said combined standard and sample by chromatography.

3. The method of claim 2 wherein said substantially purifying step comprises treating said combined standard and sample by gel permeation column chromatography.

4. The method of claim 3 wherein said substantially purifying step comprises treating said combined standard and sample by gel permeation column chromatography with a dextran gel having an exclusion volume corresponding to approximately 1,500 daltons.

5. The method of claim 1 wherein said measuring step comprises high performance liquid chromatography to measure the quantity in said substantially purified breakdown product fraction of said labelled breakdown product from said standard together with breakdown product from the sample.

6. The method of claim 1 wherein said measuring step comprises using liquid scintillation counting to measure the quantity of label in said substantially purified breakdown product fraction of said labelled breakdown product from said standard together with breakdown product from the sample.

7. A method for assessing a condition of a selected connective tissue in a body fluid from an animal, comprising providing a standard comprising the breakdown product having a radioactive label, combining a known quantity of said standard, containing a known quantity of label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step, for determining a connective tissue breakdown product in a body fluid wherein the breakdown product is known to result from breakdown of the selected connective tissue.

8. The method of claim 7 wherein the selected connective tissue contains elastin.

9. The method of claim 7 wherein the selected connective tissue contains collagen.

10. A method for assessing elastolysis in a body fluid from an animal, comprising providing a standard comprising the breakdown product having a radioactive label, combining a known quantity of said standard, containing a known quantity of label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step, for determining a connective tissue breakdown product in a body fluid wherein the breakdown product is one or both of desmosine and isodesmosine.

11. A method for assessing in a body fluid a disease process that includes destruction of a specified connective tissue component, comprising providing a standard comprising the breakdown product having a radioactive label, combining a known quantity of said standard, containing a known quantity of label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step, for determining a connective tissue breakdown product in a body fluid wherein the breakdown product is known to result from breakdown of the selected connective tissue component.

12. A method for assessing in a body fluid the efficacy of a therapy for treatment of a disease process that includes destruction of a specified connective tissue component, comprising providing a standard comprising the breakdown product having a radioactive label, combining a known quantity of said standard, containing a known quantity of label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown product fraction, whereby the proportional difference between the quantity of label in the substantially purified breakdown product fraction and the quantity of label in the known quantity of standard combined with the sample provides a measure of the proportionate loss of breakdown product during the purifying step, for determining a connective tissue breakdown product in a body fluid wherein the breakdown product is known to result from breakdown of the specified connective tissue component.

13. The method of claim 12 wherein the disease process is a disease process of chronic obstructive pulmonary disease.

14. The method of claim 12 wherein the disease process is a disease process of cystic fibrosis.

15. The method of claim 1 wherein the connective tissue breakdown product is desmosine, and said labelled breakdown product is radioactively labelled desmosine.

16. The method of claim 1 wherein the connective tissue breakdown product is pyridinoline, and said labelled breakdown product is radioactively labelled pyridinoline.

17. The method of claim 1 wherein the connective tissue breakdown product is deoxypyridinoline, and said labelled breakdown product is radioactively labelled deoxypyridinoline.

18. The method of claim 1 wherein the connective tissue breakdown product is isodesmosine and said labelled breakdown product is radioactively labelled isodesmosine.

19. A method for determining a plurality of connective tissue breakdown products in a body fluid from an animal, comprising providing a standard comprising one of said breakdown products having a radioactive label, combining a known quantity of said standard, containing a known quantity of label, with a sample of the body fluid, substantially purifying from said combined standard and sample a breakdown product fraction containing labelled breakdown product from said standard together with breakdown product from the sample, and measuring the quantity of breakdown product and the quantity of label in the substantially purified breakdown products fraction, whereby the proportional difference between the quantity of label in the substantially purified breakdown products fraction and the known quantity of label in said known quantity of standard provides a measure of the proportionate loss of breakdown products during the purifying step.

20. The method of claim 19 wherein said plurality of connective tissue breakdown products is selected from the group consisting of desmosine, isodesmosine, pyridinoline, and deoxypyridinoline.

21. The method of claim 19 wherein said standard is selected from the group consisting of desmosine, isodesmosine, pyridinoline, and deoxypyridinoline.

* * * * *